United States Patent
Kang et al.

(10) Patent No.: US 11,692,227 B2
(45) Date of Patent: Jul. 4, 2023

(54) METHOD FOR SCREENING FOR SKIN WHITENING AGENT BY USING SDF1 PROMOTER REGION

(71) Applicant: AJOU UNIVERSITY INDUSTRY-ACADEMIC COOPERATION FOUNDATION, Suwon-si (KR)

(72) Inventors: Hee Young Kang, Yongin-si (KR); Tae Jun Park, Seongnam-si (KR); Jung Eun Yoon, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 118 days.

(21) Appl. No.: 17/262,749

(22) PCT Filed: Jul. 17, 2019

(86) PCT No.: PCT/KR2019/008844
§ 371 (c)(1),
(2) Date: Jan. 25, 2021

(87) PCT Pub. No.: WO2020/022696
PCT Pub. Date: Jan. 30, 2020

(65) Prior Publication Data
US 2021/0310072 A1    Oct. 7, 2021

(30) Foreign Application Priority Data
Jul. 23, 2018    (KR) .................. 10-2018-0085397

(51) Int. Cl.
*C12Q 1/6883* (2018.01)
*C12Q 1/6876* (2018.01)
*G01N 33/50* (2006.01)

(52) U.S. Cl.
CPC ......... *C12Q 1/6883* (2013.01); *C12Q 1/6876* (2013.01); *G01N 33/5044* (2013.01); *C12Q 2600/136* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| 2014/0044799 A1* | 2/2014 | Bernerd | A61K 35/32 514/637 |
| 2017/0342496 A1* | 11/2017 | Zhang | C12Q 1/6883 |
| 2019/0075813 A1* | 3/2019 | Coquet | C12N 9/248 |

FOREIGN PATENT DOCUMENTS

| JP | 2018-027920 A | 2/2018 |
| KR | 10-2013-0056955 A | 5/2013 |

OTHER PUBLICATIONS

Yoon (Theranostics 2018, vol. 8 Issue 17 Pub Sep. 9, 2018.*
GenBank (Accession AY802782 entered Nov. 9, 2004).*
International Search Report for PCT/KR2019/008844 dated Oct. 30, 2019 from Korean Intellectual Property Office.
Belmadani, A. et al., "The chemokine SDF-1/CXCL12 regulates the migration of melanocyte progenitors in mouse hair follicles", Differentiation. 2009, vol. 77, pp. 395-411.
Karouzakis, E. et al., "DNA methylation regulates the expression of CXCL12 in rheumatoid arthritis synovial fibroblasts", Genes and Immunity. 2011, vol. 12, pp. 643-652.
NCBI. GenBank accession No. AY802782.1 (Nov. 9, 2004).
Yoon, J. E. et al., "CXCL12 negatively regulates melanigenesis via cAMP signaling pathway", In: 2017 Ajou Biomedical Conference, Poster, May 12-13, 2017, Pyeongchang, Kensington Flora Hotel.
Lee, E. et al., "CXCR7 mediates SDF1-induced melanocyte migration", Pigment Cell Melanoma Res. Sep. 2012, vol. 26, Issue 1, pp. 58-66.

* cited by examiner

*Primary Examiner* — Amanda Haney
(74) *Attorney, Agent, or Firm* — Revolution IP, PLLC

(57) ABSTRACT

A method of screening a skin whitening agent uses the stromal cell-derived factor 1 (SDF1) promoter region, the correlation between the expression amount of the skin pigment and the expression of the SDF1 promoter is observed and thus it is expected to be available in systems for pre-screening pigmentation substances and pigment reduction materials, and the drugs screened by the method is used for treatment of skin pigment-related diseases.

7 Claims, 4 Drawing Sheets
Specification includes a Sequence Listing.

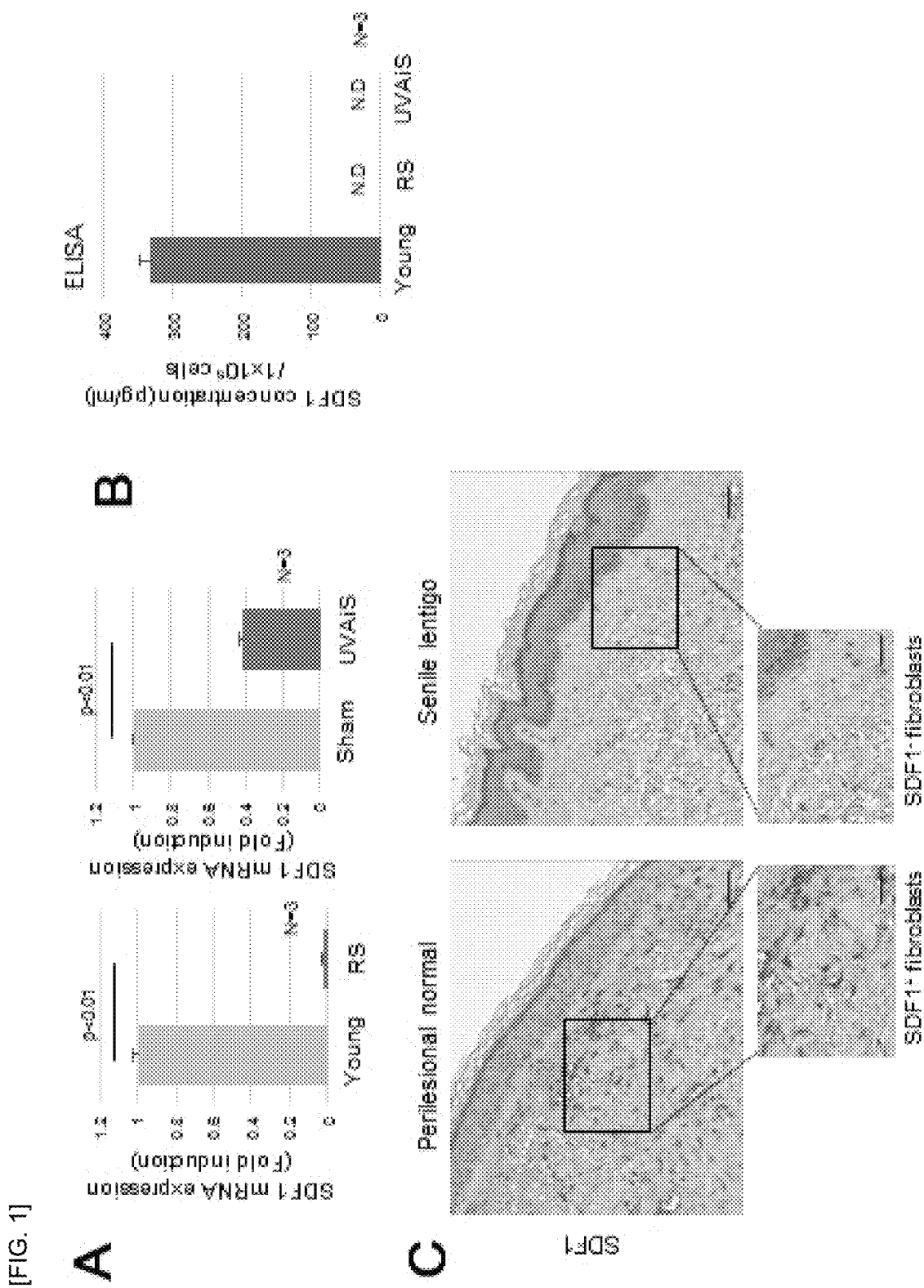
[FIG. 1]

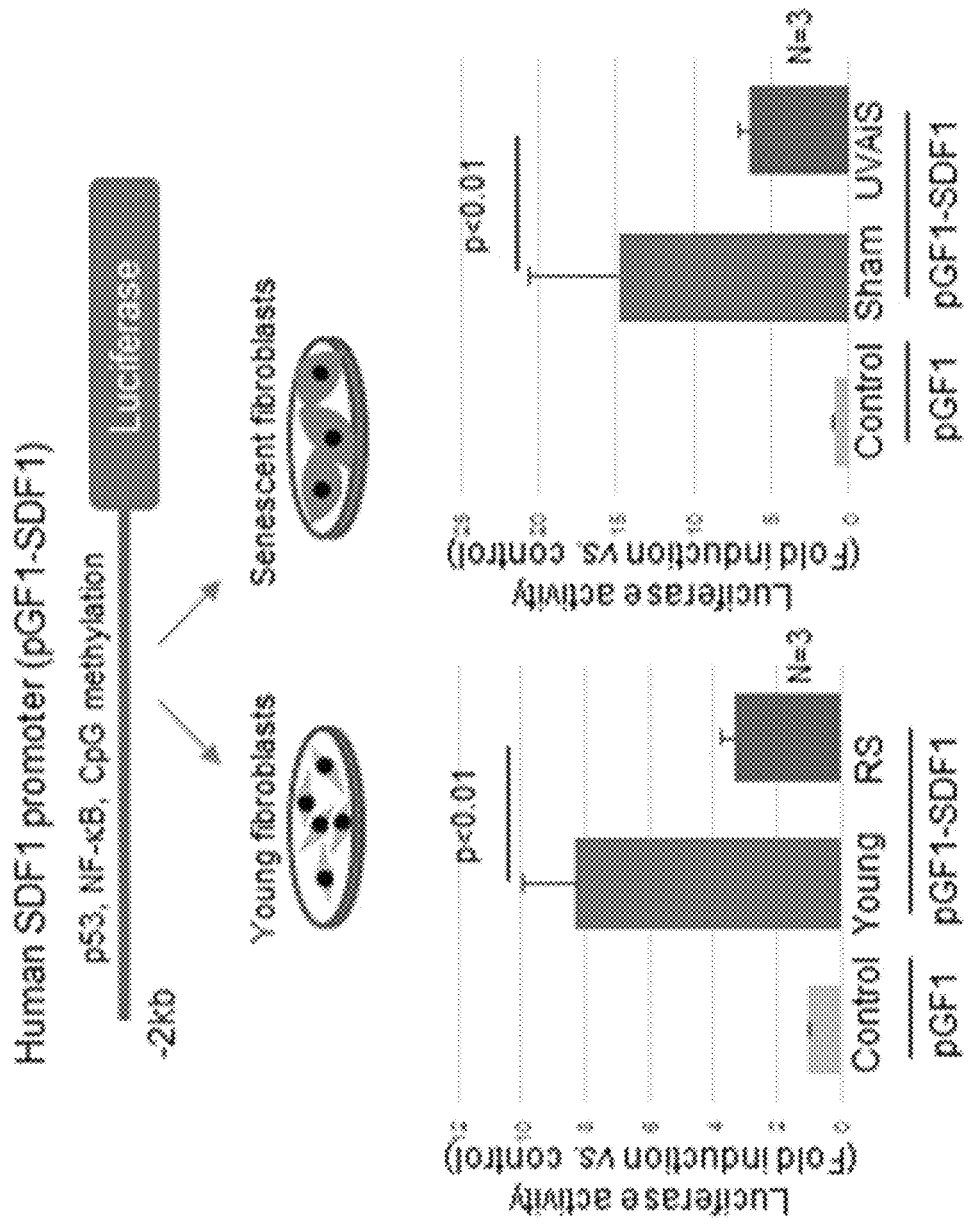
[FIG. 2]

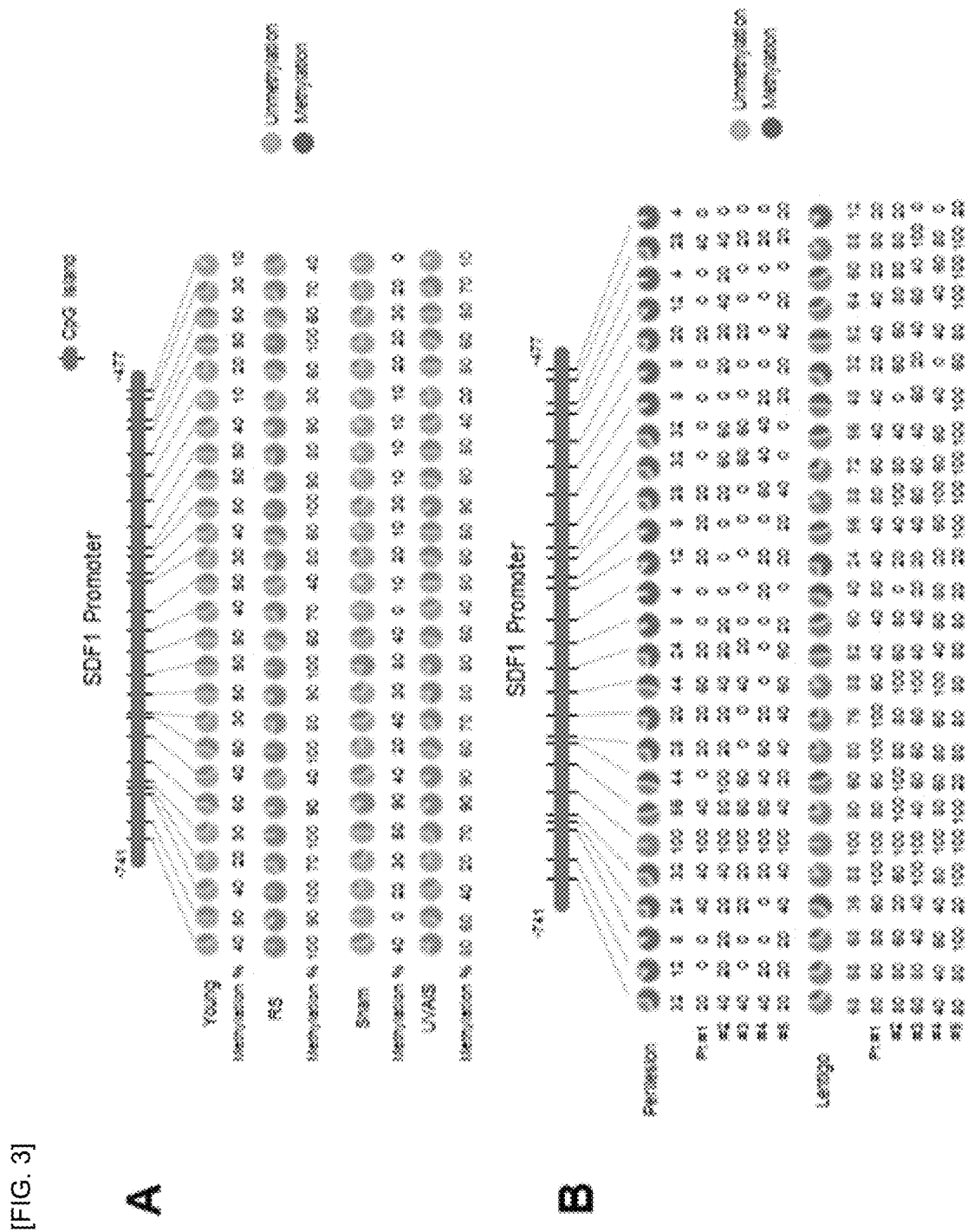
[FIG. 3]

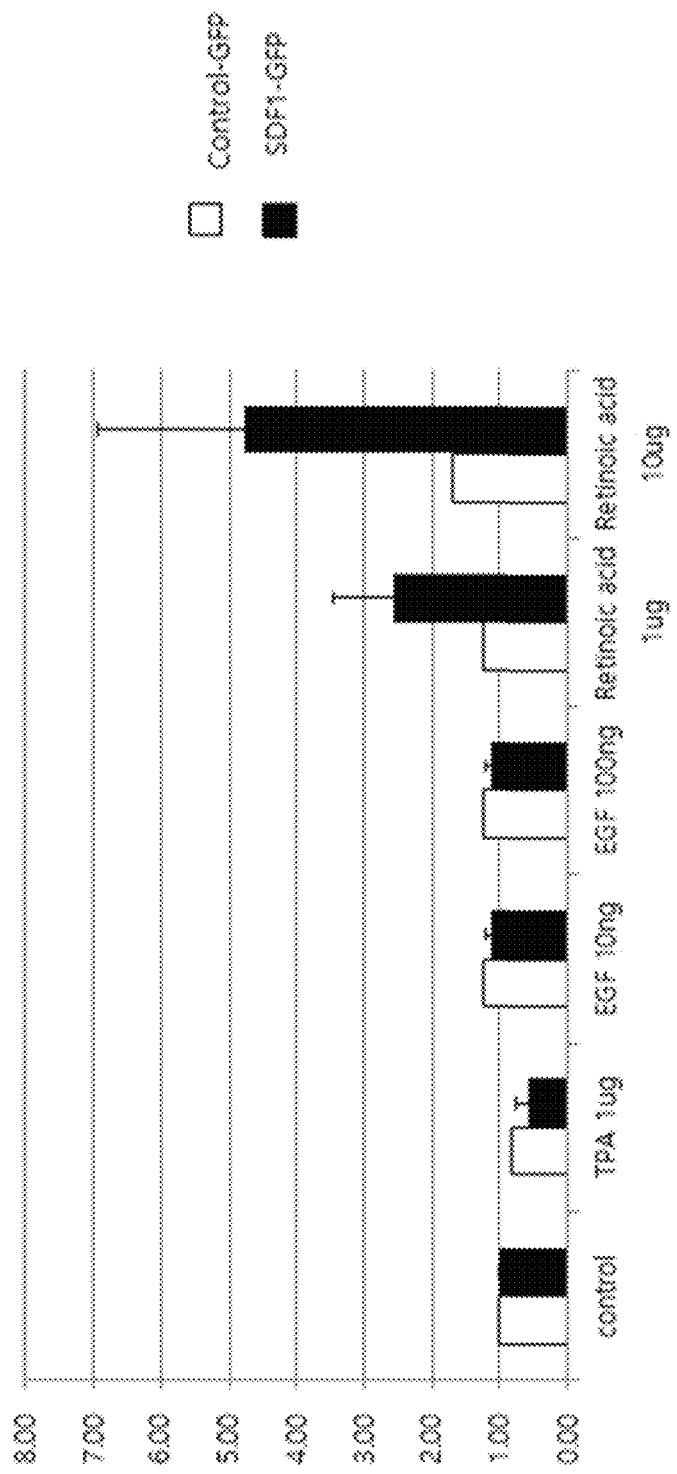
[FIG. 4]

METHOD FOR SCREENING FOR SKIN WHITENING AGENT BY USING SDF1 PROMOTER REGION

TECHNICAL FIELD

The present invention relates to a method of screening a skin whitening agent using a promoter region of stromal cell-derived factor 1 (SDF1).

BACKGROUND ART

Human skin color is determined by the amount of melanin, carotene, and hemoglobin, of which melanin acts as the most decisive factor. Melanin pigment is a phenolic polymer material in the form of a complex of black pigment and protein, and plays a role of blocking UV rays and people who lack melanin pigment are very sensitive to sunlight and are prone to burns and have a high probability of developing skin cancer even at a young age. On the other hand, short-wavelength UV rays and carcinogens form harmful free radicals in the skin and melanin plays a useful role in protecting proteins and genes by removing these free radicals. Therefore, a high amount of melanin means that there is an effective response system that can protect the skin from physical or chemical toxins.

Melanin is produced from tyrosine through a complicated process by the action of tyrosinase present in pigment cells. At this time, the produced melanin is delivered to the skin cells and exhibits a circulating action in which melanin is lost and destroyed along with epidermal detachment. This melanogenesis process is a naturally occurring phenomenon, and overproduction of melanin does not occur in normal skin. However, when the skin responds to external stimuli, such as ultraviolet rays, environmental pollution or stress, melanin is produced excessively and cannot be discharged outside the skin and is delivered to keratinocytes and accumulates in the epidermal layer of the skin, causing serious cosmetic problems such as melasma, freckles and senile blacks, as well as promoting skin aging and causing skin cancer. It is known that pigmentation occurs a lot in senile lentigo and there is a growing interest in factors that can control skin aging or pigmentation.

DISCLOSURE

Technical Problem

An object of the present invention is to provide a method of screening a skin whitening agent or a method of screening a therapeutic agent for skin pigmentation disease comprising contacting a test substance with a cell transfected with a recombinant expression vector comprising an SDF1 promoter region and a reporter gene and measuring the activity of the reporter gene.

In addition, an object of the present invention is to provide a method of screening a skin whitening agent or a method of screening a therapeutic agent for skin pigmentation disease comprising measuring the methylation level of a SDF1 promoter region in hyperpigmentary skin cells contacted with a test substance.

Technical Solution

In order to achieve the above object, the present invention provides a method of screening skin whitening agent comprising: contacting a test substance with a cell transfected with a recombinant expression vector comprising a stromal cell-derived factor 1 (SDF1) promoter region and a reporter gene; measuring activity of the reporter gene in cells contacted with the test substance; and selecting a test substance having an increased activity of the reporter gene compared to a control sample.

Also, the present invention provides a method of screening skin whitening agent comprising: contacting a test substance with hyperpigmentary skin cells; measuring methylation level of SDF1 promoter region in the hyperpigmentary skin cells contacted with the test substance; and selecting a test substance having a reduced methylation level of the SDF1 promoter region compared to a control sample.

In addition, the present invention provides a method of screening a therapeutic agent for skin pigmentation disease comprising: contacting a test substance with a cell transfected with a recombinant expression vector containing an SDF1 promoter region and a reporter gene; measuring the activity of a reporter gene in cells contacted with the test substance; and selecting a test substance having an increased activity of the reporter gene compared to a control sample.

Furthermore, the present invention provides a method of screening a therapeutic agent for skin pigmentation disease comprising: contacting a test substance with hyperpigmentary skin cells; measuring a methylation level of a SDF1 promoter region in hyperpigmentary skin cells contacted with the test substance; and selecting a test substance having a reduced methylation level of the SDF1 promoter region compared to a control sample.

Advantageous Effects

The present invention relates to a method of screening a skin whitening agent using the stromal cell-derived factor 1 (SDF1) promoter region, and the correlation between the expression amount of the skin pigment and the expression of the SDF1 promoter can be observed and thus it is expected to be available in systems for pre-screening pigmentation substances and pigment reduction materials. In addition, the drugs screened by the present invention can be used for treatment of skin pigment-related diseases.

DESCRIPTION OF DRAWINGS

FIG. 1 shows a result of measuring the expression of SDF1 in fibroblasts, FIG. 1A shows a result of real-time PCR analysis, FIG. 1B shows a result of ELISA analysis, and FIG. 10 shows a result of immunochemical staining analysis.

FIG. 2 shows a result of observing the activity of the SDF1 promoter through Luciferase assay by infecting fibroblasts, aged fibroblasts, and UVA J/cm$^2$ irradiated fibroblasts with plasmid into which the pGF-1 vector with the SDF1 promoter inserted.

FIG. 3 shows a result of analyzing methylation in fibroblasts, FIG. 3A shows a result of analyzing methylation in fibroblasts and fibroblasts that induce aging, and FIG. 3B shows a result of analyzing methylation in surrounding tissues and lentigo.

FIG. 4 shows that a vector virus (GFP vector virus) into which the SDF1 promoter was inserted, was infected and only infected fibroblasts were selected to create a cell line. It shows a result of observing the expression level of the SDF1 promoter when this cell line was treated with TPA known as a pigmentation substance, retinoic acid as a pigment inhibitor, and EGF related to skin function, respectively. FIG. 4A shows a result of measuring the degree of activity of GFP by Luciferase assay.

BEST MODE

The present invention provides a method of screening skin whitening agent comprising: contacting a test substance with a cell transfected with a recombinant expression vector comprising a stromal cell-derived factor 1 (SDF1) promoter region and a reporter gene; measuring activity of the reporter gene in cells contacted with the test substance; and selecting a test substance having an increased activity of the reporter gene compared to a control sample. Preferably, the cell may be fibroblasts, but it is not limited thereto.

In addition, the present invention provides a method of screening skin whitening agent comprising: contacting a test substance with hyperpigmentary skin cells; measuring methylation level of SDF1 promoter region in the hyperpigmentary skin cells contacted with the test substance; and selecting a test substance having a reduced methylation level of the SDF1 promoter region compared to a control sample.

In the present invention, the SDF1 promoter region may be a CpG island region of the SDF1 transcription start site (TSS), and the SDF1 promoter region may be represented by SEQ ID NO: 1, but it is limited thereto.

In addition, the present invention provides a method of screening a therapeutic agent for skin pigmentation disease comprising: contacting a test substance with a cell transfected with a recombinant expression vector containing an SDF1 promoter region and a reporter gene; measuring the activity of a reporter gene in cells contacted with the test substance; and selecting a test substance having an increased activity of the reporter gene compared to a control sample. Preferably, the cell may be fibroblasts, but it is not limited thereto.

In addition, the present invention provides a method of screening a therapeutic agent for skin pigmentation disease comprising: contacting a test substance with hyperpigmentary skin cells; measuring a methylation level of a SDF1 promoter region in hyperpigmentary skin cells contacted with the test substance; and selecting a test substance having a reduced methylation level of the SDF1 promoter region compared to a control sample.

In the present invention, the skin pigmentation disease may be selected from the group consisting of melasma, freckles, lentigo, nevus, pigmentation by drugs, pigmentation after inflammation and hyperpigmentation incurred from dermatitis, but it is not limited thereto.

In the present invention, the SDF1 promoter region may be a CpG island region of the SDF1 transcription start site (TSS), and the SDF1 promoter region may be represented by SEQ ID NO: 1, but it is limited thereto.

"SDF1 gene or protein encoded by the gene" of the present invention may be NCBI accession no. AY802782, but it is not limited thereto.

"SDF1" of the present invention may be referred to as "C-X-C motif chemokine 12 (CXCL12)".

In the present invention, "vector" refers to a DNA molecule that replicates itself used to carry a clonal gene (or another fragment of clonal DNA).

In the present invention, "expression vector" refers to a recombinant DNA molecule comprising a target coding sequence and an appropriate nucleic acid sequence essential for expressing a coding sequence operably linked in a specific host organism. The expression vector may preferably include at least one selectable marker. The marker is typically a nucleic acid sequence having properties that can be selected by a chemical method, and it corresponds to all genes capable of distinguishing a transformed cell from a non-transformed cell. Examples include antibiotic resistance genes such as Ampicillin, Kanamycin, Geneticin (G418), Bleomycin, Hygromycin and Chloramphenicol, but they are not limited thereto and can be appropriately selected by those skilled in the art.

In the present invention, the "reporter" is a protein or reporter that emits light in a living body, and includes a green fluorescent protein (GFP), a yellow fluorescent protein (YFP), or a red fluorescent protein (RFP) and the like, and preferably may be a green fluorescent protein (GFP) described in an embodiment of the present invention, but it is not limited thereto.

The term of "test substance" used in referring to the screening method of the present invention means an unknown candidate substance used in screening to examine whether it affects the expression amount of a gene or affects the expression or activity of a protein. Such sample includes chemicals, nucleotides, antisense-RNA, siRNA (small interference RNA) and natural extracts, but it is not limited thereto.

Hereinafter, the present invention will be described in more detail through examples. These examples are only intended to illustrate the present invention in more detail, and it will be apparent to those skilled in the art that the scope of the present invention is not limited by these examples according to the gist of the present invention.

Experimental Example

The following experimental examples are intended to provide experimental examples commonly applied to each of the examples according to the present invention.

1. Measurement of SDF1 Expression by Inducing Aging in Fibroblasts

In culturing fibroblasts, incubation is performed by adding 10% FBS to DMEM (high glucose content) culture solution. The doubling time of fibroblasts was approximately 24 hours, and it was continuously cultured for a doubling time of about 14 days to produce proliferative senescent fibroblasts.

In the case of UVA-induced senescent fibroblasts, the fibroblasts were washed with PBS and the culture medium was freshly changed with PBS, and then aging was induced by irradiation with 5 J/cm$^2$ UVA (wavelength 320-400 nm, maximum peak 350 nm). LZC-1 photoreactor system (Luzchem Research Inc. Ontario, Canada) was used. Sham-irradiated fibroblasts are placed in an irradiator box without UV irradiation. After irradiation, the fibroblasts are cultured for 7 days and then the experiment is conducted.

2. Observation of Expression Level of SDF1

(1) Real-Time PCR

RNA was extracted from melanocytes infected with each vector virus using RNeasy Mini Kit (Qiagen Inc., USA), and cDNA was produced using Superscript III reverse transcription system (Invitrogen, USA) using 1 μg of the extracted total RNA.

Real-time PCR (Real-time PCR) was performed with a primer corresponding to SDF1 using 2 μl of cDNA of each of the prepared experimental groups as a template.

The SDF1 primers used were (forward) 5'-

```
                                        (SEQ ID NO: 2)
TGCCAGAGCCAACGTCAAG-3'
``` and (reverse) 5'-

```
                                        (SEQ ID NO: 3)
CAGCCGGGCTACAATCTGAA-3',
``` and PCR was performed for 18s gene of each cell line as a control.

Reaction cycles of 39 repetition was performed under PCR conditions of 95° C. for 3 minutes, 95° C. for 10 seconds and 60° C. for 30 seconds and was reacted at 95° C. for 10 seconds, 65° C. for 5 seconds, and 95° C. for 5 seconds for final elongation.

(2) ELISA

The amount of secretion of SDF1 in the culture medium in which the cells were cultured was performed according to the instructions using the SDF1 ELISA kit (R&D Systems, Minneapolis, Minn.). The cells were cultured and the culture medium cultured for 48 hours was harvested, and when harvesting, the total number of cells was corrected based on the number of cells of $1 \times 10^5$ to measure the value.

(3) Immunochemical Staining

Immunochemical staining was performed with 4-μm-thick paraffin-treated tissue fragments. As the primary antibody, SDF1 (MAB350, R&D System) was diluted 1:100 in an antibody diluent.

3. SDF1 Promoter GFP Virus and GFP Virus Preparation

In order to express the SDF1 promoter gene, the SDF1 promoter gene was inserted into pGF1-vector to construct the SDF1 promoter GFP vector. In order to produce the virus into which the constructed vector was inserted, a virus production system of lentivirus was used. PVSV-G (SystemBiosciences, USA) encoding the required structural protein, the pGF1 vector into which the SDF1 promoter gene was inserted, and pGag-pol were simultaneously co-transfected into HEK-293TN cells by a liposome method. After 6 hours, the medium was replaced with a new medium, cultured for 48 hours, and the medium containing the virus was harvested, and the harvested virus was used for fibroblasts infection. As for the infected fibroblasts, only cells infected by Puromycin were selected for the experiment.

In order to confirm the expression of the prepared SDF1 promoter, Luciferase assay, an experiment that can confirm the level of GFP, was conducted to observe the expression level.

As a result, as shown in FIG. 2, the expression levels of fibroblasts infected with the vector virus into which the SDF1 promoter gene is inserted and aging-induced fibroblasts can be observed by a Luciferase assay.

4. Methylation Analysis of SDF1 Promoter in Senescent Fibroblasts and Senescent Pigmented Tissues PCR was performed on gDNA (1 ug) treated with bisulfate. PCR was performed at 94° C., 3 min; 94° C., 30 s, 52° C., 40 s, 72° C., 30 s×35; and 72° C., 3 min. Primers were constructed with the SDF1 CpG island promoter (−741 to −477; SEQ ID NO: 1). The sequences of the primers are (forward) 5'-

```
                                        (SEQ ID NO: 4)
GTTTGTGATTAGTTTATTTTATTA-3
``` and (reverse) 5'-

```
                                        (SEQ ID NO: 5)
CTAAATAAAAACCAATAAAAAAC-3'.
```

PCR products were put into blunt TOPO vectors (MGmed, Seoul, Korea), and CpG island methylation was analyzed by sequencing from genes extracted from 10 colonies in cells and 5 colonies in tissues.

5. Screening of Pigment Regulators Using SDF1 Promoter

Cells were cultured in 12 well plates in an amount of $1 \times 10^3$, and after 24 hours, 1 ug of TPA, 10 ng and 100 ng of EGF, and 1 ug and 10 ug of retinoic acid were treated, respectively. 24 hours after treatment with the drug, the activity of GFP was measured through Luciferase assay.

As a result, the SDF1 promoter activity decreased in the case of treatment with the pigmented substance TPA, and the activity of the SDF1 promoter was increased in the case of treatment with the pigment inhibitory substance retinoic acid.

Example

The basic expression level of SDF1 was remarkably low in aged fibroblasts, and it was also remarkably low in aged pigmented lesions (FIG. 1).

The expression level in fibroblasts infected with the virus produced by inserting the SDF1 promoter into the pGF1 vector was measured by Luciferase assay and it was observed that the activity was low in the aged fibroblasts (FIG. 2).

It was observed that methylation of the SDF1 promoter was significantly increased in aged fibroblasts, and it was also observed that methylation of the SDF1 promoter was also increased in senescent pigmented lesions (FIG. 3).

When the drug was screened through a cell line created by infecting fibroblasts by inserting the SDF1 promoter into the pGF1 vector, it was observed that the expression level decreased when the pigmented substance TPA was treated, and the expression level increased by retinoic acid. (FIG. 4).

Based on these results, it is possible to observe the correlation between the amount of pigmentation in the skin and the expression of the SDF1 promoter, and through this, it is expected that it can be used in a system that screens for pigmentation substances and pigment reduction substances in advance.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of screening skin whitening agent comprising:
   contacting a test substance with hyperpigmentary skin cells;
   measuring a methylation level of a SDF1 promoter region in the hyperpigmentary skin cells contacted with the test substance by a real-time PCR assay using a primer pair comprising a forward primer consisting of SEQ ID NO: 4 and a reverse primer consisting of SEQ ID NO: 5; and
   selecting a test substance that reduces the methylation level of the SDF1 promoter region compared to a control sample.

2. The method of screening skin whitening agent of claim 1, wherein the SDF1 promoter region is a CpG island region of an SDF1 transcription start site (TSS).

3. The method of screening skin whitening agent of claim 1, wherein the SDF1 promoter region is represented by SEQ ID NO: 1.

4. A method of screening a therapeutic agent for skin pigmentation disease comprising:
   contacting a test substance with hyperpigmentary skin cells;
   measuring a methylation level of a SDF1 promoter region in hyperpigmentary skin cells contacted with the test substance by a real-time PCR assay using a primer pair comprising a forward primer consisting of SEQ ID NO: 4 and a reverse primer consisting of SEQ ID NO: 5; and
   selecting a test substance that reduces the methylation level of the SDF1 promoter region compared to a control sample.

5. The method of screening a therapeutic agent for skin pigmentation disease of claim 4, wherein the SDF1 promoter region is a CpG island region of an SDF1 transcription start site (TSS).

6. The method of screening a therapeutic agent for skin pigmentation disease of claim previously presented 4, wherein the SDF1 promoter region is represented by SEQ ID NO: 1.

7. The method of screening a therapeutic agent for skin pigmentation disease of claim previously presented 4, wherein the skin pigmentation disease is selected from the group consisting of melasma, freckles, lentigo, nevus, pigmentation by drugs, pigmentation after inflammation and hyperpigmentation incurred from dermatitis.

* * * * *

SEQUENCE LISTING

<160> NUMBER OF SEQ ID NOS: 5

<210> SEQ ID NO 1
<211> LENGTH: 264
<212> TYPE: DNA
<213> ORGANISM: Homo sapiens

<400> SEQUENCE: 1

```
tacattcgct tttactgaga gccgccggcg ccttctgctt tgtttgtaca ggcgaggaaa    60
ctgaggctcg gctggtggcg ccgtgggctt ggagtccgag ccacgctgac tgcaaagacg   120
ggtctcattc ccgcagatcg agctctgccg gcggctgcgc cgcaagccgg gcaggtggcg   180
agcttgagcc cccacgcaca gaaagcagga cccctcggc tgccttgggc cgccaccgcc    240
agcaggccct ccgcccggga ctaa                                          264
```

<210> SEQ ID NO 2
<211> LENGTH: 19
<212> TYPE: DNA
<213> ORGANISM: Artificial Sequence
<220> FEATURE:
<223> OTHER INFORMATION: Primers (forward)

<400> SEQUENCE: 2

```
tgccagagcc aacgtcaag                                                 19
```

<210> SEQ ID NO 3
<211> LENGTH: 20
<212> TYPE: DNA
<213> ORGANISM: Artificial Sequence
<220> FEATURE:
<223> OTHER INFORMATION: Primers (reverse)

<400> SEQUENCE: 3

```
cagccgggct acaatctgaa                                                20
```

<210> SEQ ID NO 4
<211> LENGTH: 24
<212> TYPE: DNA
<213> ORGANISM: Artificial Sequence
<220> FEATURE:
<223> OTHER INFORMATION: Primers (forward)

<400> SEQUENCE: 4

```
gtttgtgatt agtttatttt atta                                           24
```

<210> SEQ ID NO 5
<211> LENGTH: 23
<212> TYPE: DNA
<213> ORGANISM: Artificial Sequence
<220> FEATURE:
<223> OTHER INFORMATION: Primers (reverse)

<400> SEQUENCE: 5

```
ctaaataaaa accaataaaa aac                                            23
```